US00PP13244P2

(12) United States Plant Patent
de Jong

(10) Patent No.: US PP13,244 P2
(45) Date of Patent: Nov. 19, 2002

(54) SYMPHORICARPOS PLANT NAMED 'SCARLET PEARL'

(75) Inventor: Jan de Jong, Heelsum (NL)

(73) Assignee: Gebr, Kolster B.V., Boskoop (NL)

( * ) Notice: Subject to any disclaimer, the term of this patent is extended or adjusted under 35 U.S.C. 154(b) by 0 days.

(21) Appl. No.: 10/006,805

(22) Filed: Dec. 5, 2001

(51) Int. Cl.[7] ..... A01H 5/00
(52) U.S. Cl. ..... Plt./226
(58) Field of Search ..... Plt./226

*Primary Examiner*—Kent L. Bell
(74) *Attorney, Agent, or Firm*—C. A. Whealy

(57) ABSTRACT

A new and distinct cultivar of Symphoricarpos plant named 'Scarlet Pearl', characterized by its upright and outwardly spreading plant habit; dark green leaves; large red purple-colored fruits; and good postproduction longevity.

2 Drawing Sheets

BOTANICAL CLASSIFICATION/CULTIVAR DESIGNATION

*Symphoricarpos albus* cultivar 'Scarlet Pearl'.

BACKGROUND OF THE INVENTION

The present Invention relates to a new and distinct cultivar of Symphoricarpos plant, botanically known as *Symphoricarpos albus*, commercially used as cut stems with fruits, and hereinafter referred to by the name 'Scarlet Pearl'.

The new Symphoricarpos is a product of a planned breeding program conducted by the Inventor in Wageningen, The Netherlands. The objective of the breeding program was to develop cut Symphoricarpos cultivars with attractive fruit coloration.

The new cultivar originated from a cross made by the Inventor in 1994 of two unidentified proprietary seedling selections, not patented. The cultivar 'Scarlet Pearl' was discovered and selected by the Inventor in 1994 as a flowering plant within the progeny of the stated cross in a controlled environment in Wageningen, The Netherlands.

Asexual reproduction of the new Symphoricarpos by terminal cuttings taken at Boskoop, The Netherlands, has shown that the unique features of this new Symphoricarpos are stable and reproduced true to type in successive generation of asexual reproduction.

SUMMARY OF THE INVENTION

The following traits have been repeatedly observed and are determined to be the unique characteristics of 'Scarlet Pearl'. These characteristics in combination distinguish 'Scarlet Pearl' as a new and distinct cultivar:

1. Upright and outwardly spreading plant habit.
2. Dark green leaves.
3. Large red purple-colored fruits.
4. Good postproduction longevity.

Plants of the new Symphoricarpos differ from plants of the parent seedling selections primarily in growth habit and fruit coloration.

Plants of the new Symphoricarpos can be compared to plants of the Symphoricarpos cultivar 'Mother of Pearl', not patented. In side-by-side comparisons conducted in Boskoop, The Netherlands, plants of the new Symphoricarpos differed from plants of the cultivar 'Mother of Pearl' in the following characteristics:

1. Plant of the new Symphoricarpos were more freely branching than plants of the cultivar 'Mother of Pearl'.
2. Plants of the new Symphoricarpos had darker green-colored leaves than plants of the cultivar 'Mother of Pearl'.
3. Plants of the new Symphoricarpos were more freely flowering than plants of the cultivar 'Mother of Pearl'.
4. Fruits of plants of the new Symphoricarpos were darker pink in color than fruits of plants of the cultivar 'Mother of Pearl'.

BRIEF DESCRIPTION OF THE PHOTOGRAPHS

The accompanying colored photographs illustrate the overall appearance of the new Symphoricarpos, showing the colors as true as it is reasonably possible to obtain in colored reproductions of this type. Colors in the photographs may differ slightly from the color values cited in the detailed botanical description which accurately describe the colors of the new Symphoricarpos.

The photograph on the first sheet comprises a side perspective view of a typical plant of 'Scarlet Pearl' with fruits.

The photograph at the top of the second sheet is a close-up view of upper surfaces of typical leaves of 'Scarlet Pearl'.

The photograph at the bottom of the second sheet comprises a close-up view of typical fruits of 'Scarlet Pearl'.

DETAILED BOTANICAL DESCRIPTION

The new Symphoricarpos has not been observed under all possible environmental conditions. The phenotype may vary somewhat with variations in environment such as temperature, daylength and light intensity, without, however, any variance in genotype.

The aforementioned photographs, following observations and measurements describe plants grown in Boskoop, The Netherlands, in an outdoor nursery and under commercial production practices. Plants were about three years old and pruned annually. The photographs and description were taken during the summer when outdoor day temperatures ranged from 14 to 27° C. and day temperatures ranged from 7 to 12° C. In the following dexcription, color references are made to The Royal Horticultural Society Colour Chart, 2001 Edition, except where general terms of ordinary dictionary significance are used.

Botanical classification: *Symphoricarpos albus* cultivar 'Scarlet Pearl'.

Parentage:

*Female parent.*—Unidentified proprietary selection of *Symphoricarpos albus*, not patented.

*Male parent.*—Unidentified proprietary selection of *Symphoricarpos albus*, not patented.

Propagation:

*Type.*—Terminal cuttings.

*Time to produce a rooted cutting.*—Summer: About 30 days at 12° C. Winter: About 55 days at 10° C.

*Time to produce a rooted young plant.*—About 90 days at 12° C.

*Root description.*—Freely branching; thick; light brown in color.

Plant description:

*Plant form.*—Upright and outwardly spreading perennial shrub; broad inverted triangle.

*Growth habit.*—Moderately vigorous. Freely branching; dense and bushy growth habit.

*Plant height.*—About 90 cm.

*Plant width* (*spread*).—About 125 cm.

*Quantity of stems per year.*—About 20.

*Lateral branches.*—Length: About 17 cm. Diameter: About 2 mm. Internode length: About 2.1 cm. Strength: Strong. Texture: Smooth. Color: Young stems: 175B. Mature stems: 199A.

*Foliage description.*—Leaves opposite, simple and generally symmetrical. Length: About 3.5 cm. Width: About 3.5 cm. Shape: Broadly elliptic to orbicular. Apex: Obtuse to slightly retuse. Base: Obtuse. Margin: Mostly entire; older leaves may be lobed. Texture: Glabrous; very slightly rugose. Venation pattern: Pinnate. Color: Developing leaves, upper surface: 137A. Developing leaves, lower surface: 137D. Fully expanded leaves, upper surface: 139A. Fully expanded leaves, lower surface: N138B. Venation, upper surface: 138A. Venation, lower surface: 138C. Petiole: Length: About 3 mm. Diameter: About 1 mm. Texture: Pubescent. Color: 143A.

Flower description:

*Flower type and habit.*—Small white and pink-colored single campanulate flowers arranged in terminal and axillary clusters with about 20 flowers per cluster; about 80 flowers and flower buds per lateral branch. Flowers not fragrant. Flowers not persistent. Flowers face outward to slightly drooping.

*Natural flowering season.*—Late summer, typically August to early September in Boskoop, The Netherlands.

*Postproduction longevity.*—Cut stems are typically harvested when all flowers have developed fruits. Flowers last about three to five days on the plant. Postproduction longevity of cut stems with fruits is about two weeks.

*Flower cluster height.*—About 2.3 cm.

*Flower cluster diameter.*—About 1.8 cm.

*Flower buds.*—Height: About 5 mm. Diameter: About 3 mm. Shape: Oval to obovate. Color: 184A to 185A.

*Flowers.*—Diameter: About 5 mm. Depth: About 6 mm.

*Petals.*—Quantity per flower: Five. Length: About 5 mm. Width: About 4 mm. Shape: Oval to elliptic. Apex: Obtuse. Base: Fused. Margin: Entire. Texture: Upper surface: Pubescent. Lower surface: Glabrous. Color: Developing and fully opened flowers, upper surface: 157C; color does not fade with subsequent development. Developing and fully opened flowers, lower surface: 186C.

*Sepals.*—Quantity per flower: Five. Length: About 4 mm. Width: Less than 1 mm. Shape: Linear. Apex: Broadly acuminate. Base: Fused. Margin: Entire. Texture, upper and lower surfaces: Smooth. Color: Developing and fully expanded sepals, upper surface: 143B. Developing and fully expanded sepals, lower surface: 143A.

*Peduncles.*—Length: About 1 cm. Diameter: About 7 mm. Orientation: About 30 to 90° from vertical. Strength: Strong. Color: 175B.

*Reproductive organs.*—Stamens: Quantity per flower: About five. Anther shape: Narrowly oblong. Anther length: About 1 mm. Anther color: 159D. Pollen amount: Scarce. Pollen color: Close to 158D. Pistils: Quantity per flower: One. Pistil length: About 3 mm. Stigma shape: Club-shaped. Stigma color: 144B to 144C. Style length: About 2.5 mm. Style color: 145D. Ovary color: 143A to 143B.

*Fruits.*—Quantity per flower: One. Days to ripening: About 60. Type: Berry. Shape: Spherical. Length: About 1.2 cm. Diameter: About 1.3 cm. Texture: Smooth, glabrous. Color: Initially 68A to 68B, becoming darker, 71C to 71D, with development; glossy.

*Seeds.*—Quantity per fruit: About two per fruit. Length: About 1.5 mm. Diameter: About 1.5 mm. Texture: Smooth, glabrous. Color: 199A.

Disease/pest resistance: Plants of the new Symphoricarpos have not been observed to be resistant to pathogens and pests common to Symphoricarpos.

Temperature tolerance: Plants of the new Symphoricarpos have been observed to tolerate temperatures ranging from −15 to 35° C.

It is claimed:

1. A new and distinct cultivar of Symphoricarpos plant named 'Scarlet Pearl', as illustrated and described.

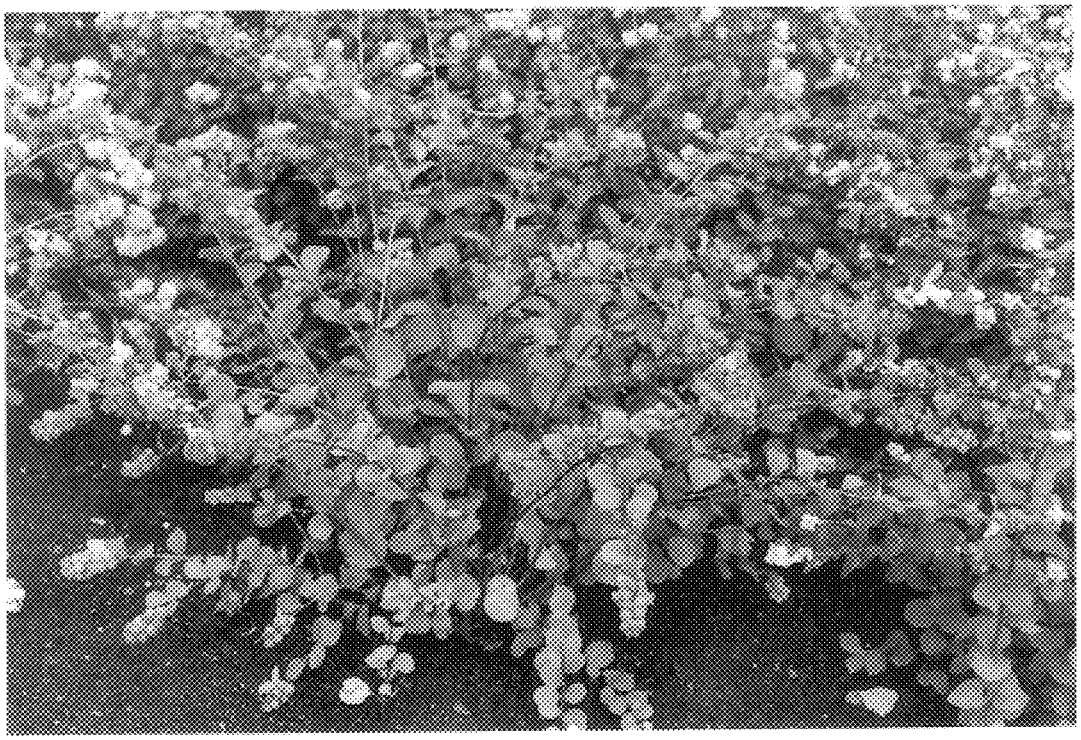

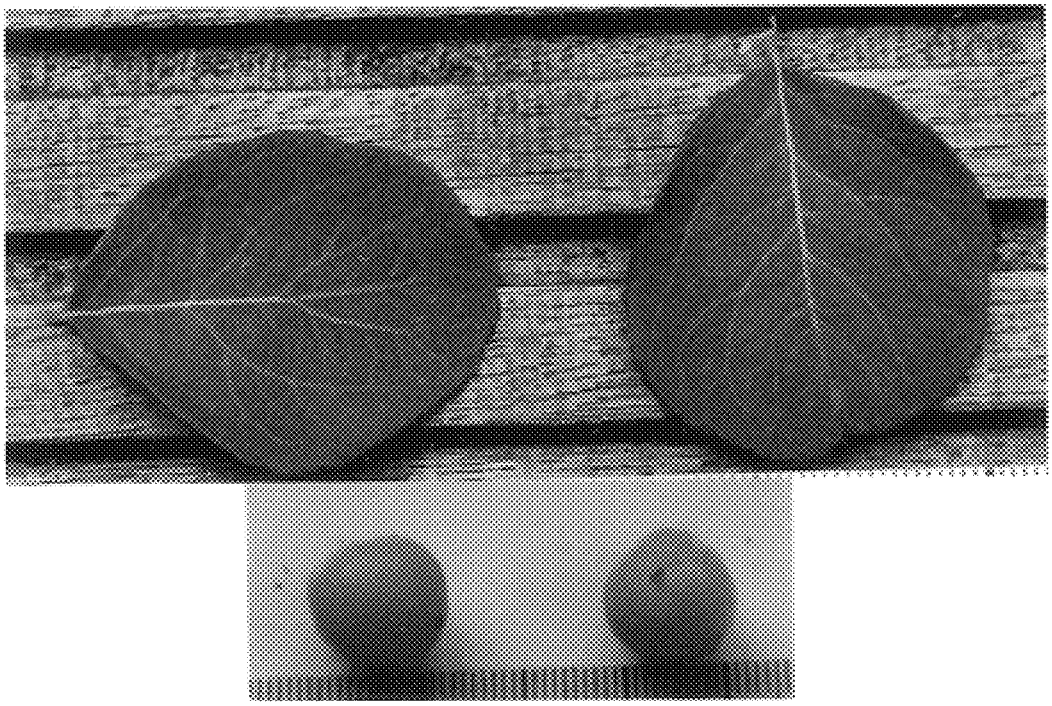

* * * * *